US009612204B2

(12) United States Patent
Locklear et al.

(10) Patent No.: US 9,612,204 B2
(45) Date of Patent: Apr. 4, 2017

(54) MEASUREMENT OF SCALE INHIBITOR IN WATER SYSTEMS

(71) Applicants: ConocoPhillips Company, Houston, TX (US); Advanced Analytical Technologies, Inc., Ankeny, IA (US)

(72) Inventors: Jay Edward Locklear, Houston, TX (US); Thomas Baugh, Houston, TX (US); Pierre Varineau, Ankeny, IA (US); Wei Wei, Ankeny, IA (US)

(73) Assignees: ConocoPhillips Company, Houston, TX (US); Advanced Analytical Technologies, Inc., Ankeny, IA (US)

( * ) Notice: Subject to any disclaimer, the term of this patent is extended or adjusted under 35 U.S.C. 154(b) by 0 days.

(21) Appl. No.: 15/167,990

(22) Filed: May 27, 2016

(65) Prior Publication Data

US 2016/0349186 A1 Dec. 1, 2016

Related U.S. Application Data

(60) Provisional application No. 62/167,448, filed on May 28, 2015.

(51) Int. Cl.
G01N 21/78 (2006.01)
G01N 21/64 (2006.01)
G01N 27/447 (2006.01)
G01N 33/18 (2006.01)
G01N 21/77 (2006.01)
C02F 5/08 (2006.01)
G01N 33/28 (2006.01)

(52) U.S. Cl.
CPC ............ G01N 21/78 (2013.01); C02F 5/08 (2013.01); G01N 21/643 (2013.01); G01N 21/6428 (2013.01); G01N 27/44726 (2013.01); G01N 33/1833 (2013.01); G01N 33/2823 (2013.01); G01N 2021/7786 (2013.01)

(58) Field of Classification Search
CPC .... G01N 33/18; G01N 33/1833; G01N 33/24; G01N 33/246; G01N 33/2823; G01N 33/2847; G01N 21/64; G01N 21/6428; G01N 21/643; G01N 21/77; G01N 2021/7786; G01N 27/447; G01N 27/44721; G01N 27/44726; C02F 5/08; C02F 5/086
USPC ........... 436/60, 79, 149, 150, 164, 172, 177; 422/82.05, 82.08; 204/450, 451, 455, 204/513, 514
See application file for complete search history.

(56) References Cited

U.S. PATENT DOCUMENTS

| 5,389,548 | A | * | 2/1995 | Hoots | ................. G01N 21/643 436/104 |
| 7,638,024 | B2 | | 12/2009 | Morita | |
| 7,943,058 | B2 | * | 5/2011 | Hills | .......................... C02F 5/12 166/279 |
| 2007/0012568 | A1 | | 1/2007 | Morita | |
| 2011/0027803 | A1 | * | 2/2011 | Moussavi | ............... C08F 2/005 435/7.9 |
| 2014/0260708 | A1 | * | 9/2014 | Harrell | ................... G01N 17/00 73/866 |
| 2015/0184069 | A1 | * | 7/2015 | Nuutinen | ............... C09K 11/06 210/700 |

OTHER PUBLICATIONS

Alshamrani et al. Abstract from Abstracts of Papers, 248th ACS National Meeting & Exposition, San Francisco, CA, United States, Aug. 10-14, 2014.*
Chilcott, SPE60194, "The development and application of an accurate assay technique for sulphonated polyacrylate co-polymer oilfield scale inhibitors", Soc. of Petrol. Eng. 2000.
Boak, SPE130401, "New Developments in the analysis of scale inhibitors", SPE Production & Operations, Nov. 2010.
Mayer, "How to increase precision in capillary electrophoresis", J. Chrom. A, 901 (2001), 21-37.

* cited by examiner

Primary Examiner — Maureen Wallenhorst
(74) Attorney, Agent, or Firm — Boulware & Valoir

(57) ABSTRACT

A method for determining a concentration of a scale inhibitor in a water system that includes contacting a scale inhibitor with a dye in a capillary channel to form a complex effective to generate fluorescence; measuring a fluorescence signal generated by the complex; and, determining the concentration of the scale inhibitor based on the fluorescence signal.

16 Claims, 3 Drawing Sheets

MEASUREMENT OF SCALE INHIBITOR IN WATER SYSTEMS

PRIOR RELATED APPLICATION

This application claims priority to U.S. Ser. No. 62/167,448, Measurement of Scale Inhibitor in Water Systems, filed May 8, 2015 and incorporated by reference herein in its entirety for all purposes.

FIELD

This disclosure relates to measurement of scale inhibitors in water systems, particularly to the quantification of anionic scale inhibitors in produced water systems.

BACKGROUND

Scale deposition is a common problem encountered in oilfield operations. Scaling can be caused by a temperature or pressure change, out-gassing, a pH shift, or mixing of incompatible waters. The deposited scale adheres on the surfaces of perforations, casing, production tubing, valves, pumps, and downhole equipment, thereby clogging the wellbore and interfering with fluid flow. Scale deposition can also harbor bacteria and facilitate corrosion.

Scale inhibitors have been used in oilfield applications to minimize or prevent scale deposition. Scale inhibitors can be deployed downhole by squeeze treatment. Additionally, scale inhibitors can be added downhole by injection through capillary strings or via the annulus and injection ports on topside processing equipment. Once introduced downhole, the scale inhibitors are adsorbed onto the rock formation and slowly released back into the water over time. Scale inhibitors prevent the nucleation of deposits and/or impede crystal growth after nucleation has occurred. Occasionally scale inhibitors can act as dispersants.

To effectively control scale deposition, the scale inhibitors have to be present above a certain concentration. The minimum inhibitor level required to prevent scale deposition is commonly referred to as "minimum inhibitory concentration" (MIC) or "minimum effective concentration" (MEC).

During oil and gas production, scale inhibitor is injected into the reservoir and allowed to return gradually. The concentration of scale inhibitors will decrease over time until such time that the concentration is below the MIC or MEC level. Once the concentration of scale inhibitors falls below the MIC or MEC level, the scale inhibitors can no longer effectively prevent scale formation. Thus, monitoring scale inhibitor residual levels from produced water is a proactive way to determine the need for additional scale inhibitor treatments or the need for changing treatment levels.

Various techniques exist for determining the level of scale inhibitors in aqueous systems. Existing methods include the Hyamine® precipitation method, the colorimetric method, and elemental analysis techniques, such as inductively coupled plasma, atomic absorption spectroscopy, atomic-emission spectroscopy, or high performance liquid chromatography.

However, multiple analytical techniques are typically needed in order to analyze the entire set of anionic scale inhibitors. In addition, analyses are often complicated by factors such as dissolved ions (i.e., chloride), high salinity, and other matrix effects such as dissolved organic compounds. The existing methods can further have one or more disadvantages including labor intensive sample preparation and analysis, long turnaround times, a requirement for excessive replicate instrumentation, and expensive and complex analytical instrumentation.

Thus, the art would be receptive to improved methods of determining the level of scale inhibitors in water systems. Advantageously, the improved methods are robust, high throughput methods capable of analyzing different classes of scale inhibitors without the need for de-salting, sample cleanup, extensive sample handling and high capital equipment investments.

SUMMARY

In an embodiment, a method for determining a concentration of a scale inhibitor in a water system comprises: contacting a scale inhibitor with a dye in a capillary channel to form a complex effective to generate fluorescence; measuring a fluorescence signal generated by the complex; and determining the concentration of the scale inhibitor based on the fluorescence signal.

In another embodiment, a method of treating a water system comprises: introducing an effective amount of a scale inhibitor to a water system; obtaining a sample of the water system containing the scale inhibitor; contacting the scale inhibitor in the sample with a dye in a capillary channel to produce a complex effective to generate fluorescence; measuring a fluorescence signal generated by the complex; determining a concentration of the scale inhibitor based on the fluorescence signal; and adding an additional quantity of a scale inhibitor to the water system if the measured concentration is below a given value.

BRIEF DESCRIPTION OF THE DRAWINGS

The invention, together with further advantages thereof, may best be understood by reference to the following description taken in conjunction with the accompanying figures by way of example and not by way of limitation, in which.

DETAILED DESCRIPTION

Figure 1:
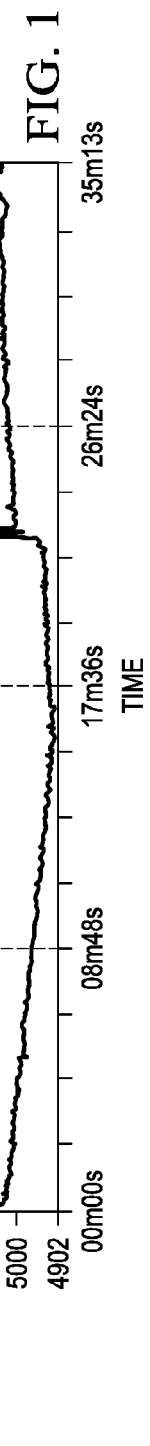
FIG. 1 shows capillary electrophoresis chromatograms of samples containing sulfonated scale inhibitors in increasing amounts of sodium chloride.

The inventors hereof have developed capillary electrophoresis methods for measuring scale inhibitor levels in water systems. The methods comprise contacting a scale inhibitor with a dye to produce a complex effective to generate fluorescence; separating the complex from an inorganic salt contained in a sample of the water system in a capillary channel; measuring a fluorescence signal generated by the complex; and determining the concentration of the scale inhibitor based on the fluorescence signal.

Advantageously, the methods can be applied to a variety of scale inhibitors including anionic polymer materials, which are usually difficult and time consuming to quantify in produced water by existing methods. In addition, the methods are sensitive and can analyze scale inhibitors at parts per million (ppm) levels.

In a further advantageous feature, capillary electrophoresis enables the measurement of scale inhibitors in the presence of dyes without the need to de-salt the sample in a separate step. Without wishing to be bound by theory, it is believed that electrophoresis separates the scale inhibitor and/or scale inhibitor/dye complex from the salts and/or interfering ions present in the sample allowing the complex to fluoresce without quenching.

The methods of the disclosure can be high-throughput, which means that rather than carrying out the analysis of the samples one after another, several samples can be analyzed simultaneously. High-throughput methods shorten the turn-around time and allow for increased experimental load without subsequently increasing costs or analysis time.

The methods are based on the discovery that a Beer-Lambert (linear) relationship exists between the concentration of the scale inhibitors and the intensity of the fluorescence emitted by the complex formed from the scale inhibitors and dyes.

The dyes are selected in such a way that they form fluorescent complexes with scale inhibitors that can be measured by fluorometry. Advantageously, the dyes have little or no intrinsic fluorescence. In other words, the dyes do not fluoresce in the absence of complexation with scale inhibitors. This is an advantageous feature because the level of background fluorescence in the absence of scale inhibitors is very low, which allows for more sensitive detection of scale inhibitors. Optionally, the dyes form fluorescent complexes with different classes of scale inhibitors so that the methods can be used to analyze different varieties of scale inhibitors.

As used herein, a complex means a chemical association of two or more species (as ions or molecules) joined by ionic bonds, covalent bonds, dipole-dipole interactions, hydrogen bonding, Van der Waals forces, or a combination comprising at least one of the foregoing. A complex of a scale inhibitor and a dye includes compounds formed from an ion or a molecule of the scale inhibitor with an ion or molecule of the dye. Suitable dyes are generally planar, aromatic, ring-shaped chromophore molecules that bind to scale inhibitors forming fluorescent complexes. Exemplary dyes include SYBR® Gold, GelStar', or a combination comprising at least one of the foregoing. Other dyes that form fluorescent complexes with scale inhibitors can also be used.

Complexation occurs during electrophoresis as the inhibitor is separated from salts. In an embodiment, a dye effective to form fluorescent complexes with the scale inhibitors is included in a chromatographic mobile phase (electrolyte) and forms fluorescent complexes with the scale inhibitors in the capillary channels during electrophoresis.

Exemplary scale inhibitors that can be analyzed by the electrophoresis methods include phosphate esters; phosphonates such as non-polymeric phosphonates and aminophosphonates; polycarboxylates such as polyacrylic acid, polyacrylate, polyaspartic acid, polyaspartate; phosphine polymers; sulfonates such as polyvinyl sulfonate, polystyrene sulfonate, and sulfonated co-polymers; polyvinyl sulfate; or a combination comprising at least one of the foregoing. In an embodiment, the scale inhibitors include an ionic inhibitor.

As used herein, the polymers can be homopolymers and copolymers.

The term "scale" refers to inorganic salts with limited solubility in water or insoluble in water. Examples include but are not limited to multi-valent salts of carbonates (e.g., $CaCO_3$, $MgCO_3$) and sulfates (e.g., $BaSO_4$, $SrSO_4$).

Any water system containing these scale inhibitors may be analyzed by the electrophoresis methods. In addition to water and the scale inhibitors, the water system optionally contains inorganic salts such as $Na_2SO_4$, $MgCl_2$, $SrCl_2$, $BaCl_2$, $CaCl_2$, KCl, NaCl, $NaHCO_3$, $Na_2CO_3$, $FeCl_2$, or a combination comprising at least one of the foregoing. In an embodiment, the water system is an oilfield fluid. Exemplary oilfield water systems can be based on seawater, formation water, produced water, a drilling fluid, a completion fluid, a stimulating fluid, or a squeezing fluid. Other industrial water systems containing scale inhibitors can also be analyzed by the methods disclosed herein.

The aqueous samples containing the scale inhibitors can be analyzed directly without any pre-treatment. In the instances where the samples contain particulate matters, the samples can be filtered first to remove the solids. For example, produced water streams may contain blends of inorganic salts, sediments, organic compounds, oils, asphaltenes, hydrocarbons, dissolved gases, cellular matter, microbes, and dead cellular matter. In an embodiment, the produced water is filtered prior to analysis in order to eliminate particulate matter.

If desirable, the water system may be diluted with water or brine to decrease the concentration of the scale inhibitors to a concentration range of interest, for example, about 0.01 ppm to 500 ppm, about 0.1 ppm to about 100 ppm, or about 0.1 ppm to about 50 ppm.

In an embodiment, the concentration of sodium chloride, sodium acetate, and sodium sulfate, or a combination thereof in a sample of the water system is less than about 15 wt. %, less than about 12 wt. %, less than about 10 wt. %, or less than about 9 wt. %, based on the total weight of the sample. In another embodiment, the sum of the weights of sodium chloride, sodium acetate, and sodium sulfate in a sample of the water system is less than about 15 wt. %, less about 12 wt. %, less than about 10 wt. %, or less than about 9 wt. %, based on the total weight of the sample.

Without wishing to be bound by theory, it is believed that the concentration of sodium chloride, sodium acetate, and sodium sulfate may influence the separation of scale inhibitors and/or their complexes with the dyes. FIG. 1 shows the effect of sodium chloride on the separation of scale inhibitors. The distance between peaks decreases as the salt concentration rises, eventually producing no separation. Accordingly, when a sample of the water system contains greater than about 15 wt. %, greater than about 12 wt. %, greater than about 10 wt. %, or greater than about 9 wt. % of sodium chloride, sodium acetate, sodium sulfate, or a combination thereof, based on the total weight of the sample, the sample may be diluted first before being analyzed.

In the methods disclosed herein, the separation and the detection of the scale inhibitors are carried out by capillary electrophoresis (CE). As used herein, the term "capillary electrophoresis" is used in its normal sense and indicates electrophoretic separation performed in relatively low volume systems. In an embodiment, capillary channels such as tubes (or capillaries) are used. Capillary tubes are typically hollow tubes having diameters of about one μm to about 500 μm.

Many materials may be used to form capillaries. In an embodiment, fused silica capillaries are used. The fused silica capillaries are optionally covered with an external protective coating to increase their mechanical strength. If desirable, the inner surface of the capillaries can be chemically modified by covalently binding (coating) different substances onto the capillary wall. These coatings are used for a variety of purposes, such as to reduce sample adsorption or to change the ionic charge on the capillary wall.

In a CE separation, a capillary is filled with an electrolyte (also referred to as a "mobile phase"). Samples can be introduced onto the capillary electrophoresis system via capillary action, pressure, siphoning, or electrokinesis. In an embodiment, samples are injected via a hydrodynamic injection (i.e. injected by vacuum). Once injected, an electrical field is applied across the capillary. The scale inhibitor/dye complex separates from inorganic salts and interfering ions as it migrates through the capillary due to the difference in their electrophoretic mobility. The separated complex is detected near the outlet end of the capillary.

The electrolyte can be a gel or a solution comprising a buffer salt and a water-soluble polymer. The pH of the electrolyte is about 7 to about 10 or about 7 to about 9, or about 7 to about 8. A small amount of 2-amino-2-hydroxymethyl-propane-1,3-diol (TRIS) can be added to the electrolyte to adjust pH. The pH adjustment can insure deprotonation of carboxylic acid containing scale inhibitors, thus allowing complexation with the dye.

The water-soluble polymer in the electrolyte includes, but are not limited to, hydroxy(propyl)methyl cellulose, hydroxyethyl cellulose, polyvinyl alcohol and polyvinylprrolidone. The water-soluble polymer is present in an amount of about 0.01 to about 10 wt %, or about 0.05 to about 5 wt. % or about 0.1 to about 3 wt %, based on the total weight of the electrolyte.

The electrolyte has a relatively low dielectric strength and can contain a buffer salt at a concentration of about 0.002 to 0.5 M. The exemplary salts include N,N-bis(2-hydroxyethyl)-2-aminoethanesulfonic acid sodium salt (BES), TRIS, and the like. In an embodiment, the dielectric strength of the electrolyte is increased by adding an additive. Advantageously, the additive increases the electrolyte's dielectric strength without increasing its conductivity, which would reduce analytical resolution. Suitable additives include amino acids such as aminocaproic acid.

Figure 2A:
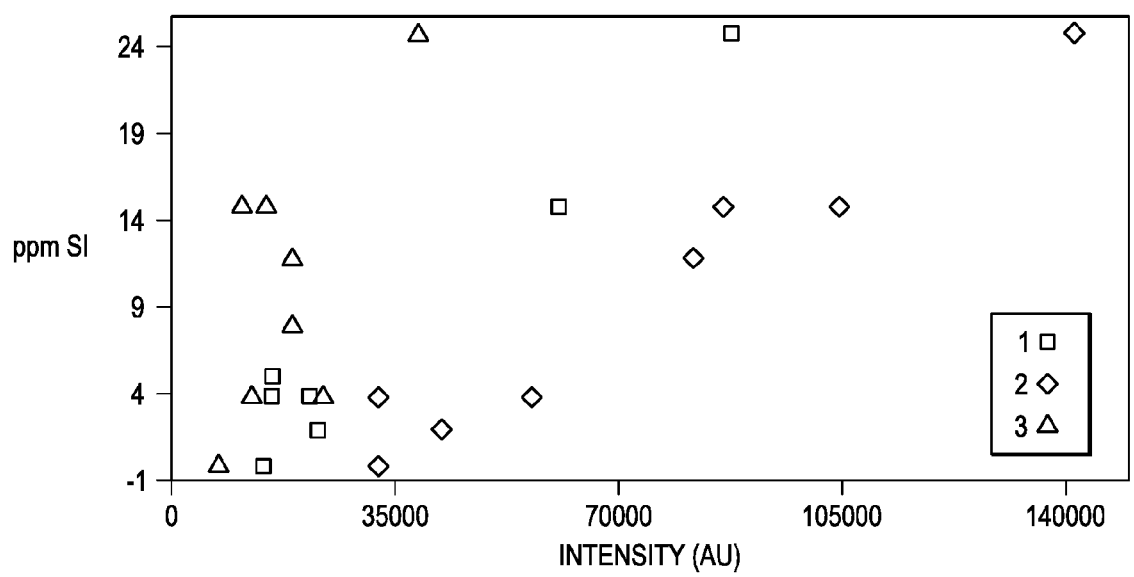
FIG. 2A shows the calibration of a sulfonated scale inhibitor-containing sample analyzed in a gel buffer having no dielectric modifier.
Figure 2B:
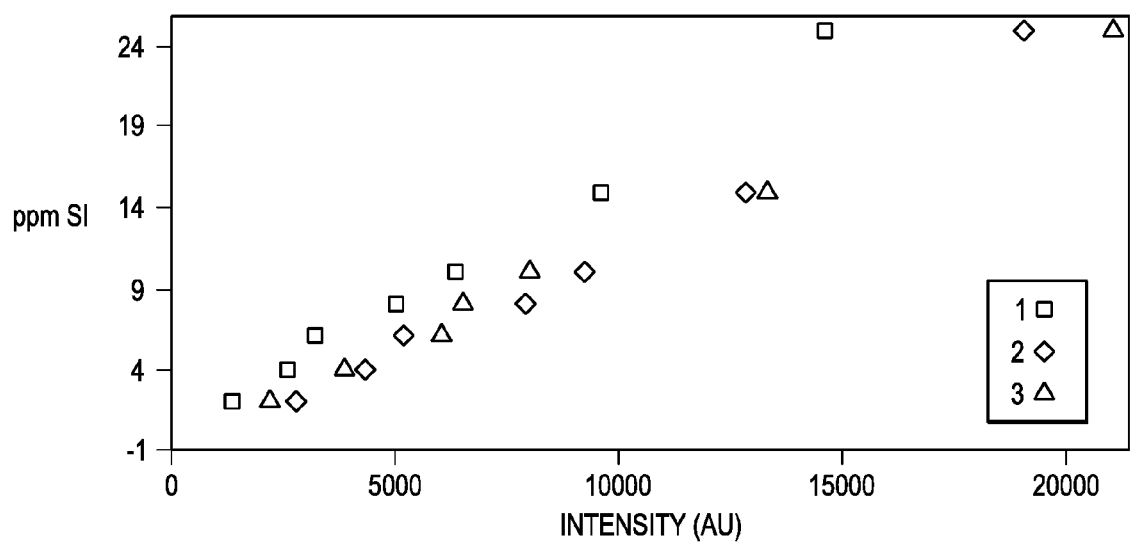
FIG. 2B shows the calibration of a sulfonated scale inhibitor-containing sample analyzed in a gel buffer containing an aminocaproic acid dielectric modifier.

The stabilizing effect of amino acids is illustrated by examining calibration curves of samples containing a sulfonated scale inhibitor on capillaries 1, 2, and 3. As shown in FIGS. 2A and 2B, correlation values can be improved from a range of 0.5 to 0.95 before stabilization to 0.85 to 0.99 after stabilization. Without wishing to be bound by theory, it is believed that on the capillary columns, salts are generally separated from the scale inhibitor and the dye but trace amounts of salt may remain on the column producing localized areas with different dielectric strengths. These areas of changing dielectric strength may affect the scale inhibitor-dye complex fluorescence intensity and produce experimental variation. Amino acids such as aminocaproic acid enhance the peak resolution and provide additional dielectric strength thereby minimizing the effects of trace salt.

The electrolyte can optionally contain an internal standard to compensate for differences in fluorescence signal intensity caused by the variation in capillary diameters and injection volumes. Suitable internal standards include, but are not limited to, fluorescein, fluorescein sulfonate, calcein, and BCECF (2',7'-bis-(2-carboxyethyl)-5-(and-6)-carboxyfluorescein).

The detection of scale inhibitor-dye complexes separated by CE may be achieved by any of the known techniques. In an embodiment, the complex is detected by a fluorometer. A fluorometer can have independent excitation and emission monochrometers, which allows for scanning of excitation wavelengths with fixed emission monitoring or a fixed excitation wavelength with scanned emission monitoring. Preferably, the emission detection is perpendicular to excitation to reduce light scattering effects.

Experiments

Synthetic field brines were used to evaluate the system. A synthetic aqueous solution, Field "A" was made by mixing pure salts with de-ionized water. Calcium chloride, sodium chloride, magnesium chloride, sodium bicarbonate, potassium chloride, sodium sulfate, and sodium carbonate were obtained from Fisher Chemicals. Strontium chloride hexahydrate, sodium acetate trihydrate, and barium chloride were obtained from Sigma-Aldrich. Formulation for synthetic field water "Field A" is shown in Table 1.

TABLE 1

|  | Field A, mg |
|---|---|
| $Na_2SO_4$ | 1036.5 |
| $MgCl_2*6H_2O$ | 1170.7 |
| $SrCl_2*6H_2O$ | 36.5 |
| $BaCl_2$ | 121.3 |
| $CaCl_2*2H_2O$ | 465.9 |
| KCl | 171.6 |
| NaCl | 23883.9 |
| $NaHCO_3$ | 1665.8 |
| $Na_2CO_3$ | 0.0 |
| $NaAc*3H_2O$ | 2304.49 |
| $FeCl_2*4H_2O$ | 0.00 |

The scale inhibitors used in the examples are described in Table 2.

TABLE 2

| Material | Chemical Description |
|---|---|
| SI-X | Sulfonated co-polymer |
| SI-A | Phosphonate |
| SI-B | Sulfonated with P-group (monomer with phosphonate moiety) |
| SI-C | Polymaleate plus homo single carboxylic acid |

The electrolyte for the capillary electrophoresis contained a buffer solution with a dissolved water-soluble polymer. The electrolyte has a pH of 8.2 to 9.0, total buffer concentrations between 0.002 to 0.50 M, and polymer concentrations between 0.1 to 3.0 weight percent. The matrix may also contain up to 250 mM amino caproic acid and 2 mM TRIS base.

Fluorescein was used as an internal standard at 5E-8M. Other internal standards used included fluorescein sulfonate, calcein, and BCECF (2',7'-bis-(2-carboxyethyl)-5-(and-6)-carboxyfluorescein).

The capillary electrophoresis system used in the examples was a modified FRAGMENT ANALYZER™ available from AATI. The system uses excitation wavelengths of 460 to 495 nm and detects fluorescence emission from 510 to 730 nm.

A Shimadzu RF 5301 fluorometer was used to evaluate the fluorescence emission spectra of various scale inhibitor-dye complexes.

A UVP Bioimaging Systems Digi-Doc-It System was used to qualitatively screen scale inhibitor-dye interaction via fluorescence emission.

Sample 1

The affinity of dye SYBR® Gold towards scale inhibitor SI-X was examined. Tests were conducted in deionized water. Four samples were prepared. Well 1 contained 100 μl of 1 μL of SYBR® Gold per 10 mL DI water. Well 2 contained 100 μl of well 1 solution with 10 ppm SI-X added. Wells 3 and 4 contained 100 μL of well 1 solution with 1 ppm of SI-X added. The samples were examined by a UVP Bioimaging Systems Digi-Doc-It System. Well 1 did not show fluorescence indicating that SYBR® Gold does not fluorescence in the absence of scale inhibitor. Well 2 showed significant fluorescence and wells 3 and 4 showed weaker fluorescence. The results indicate that SI-X and SYBR® Gold form a fluorescent complex with no background fluorescence in the absence of scale inhibitor.

Sample 2

SYBR® Gold, YOYO-1, TOTO-3, TOTO-1, POP-3 iodide, YOYO-3 iodide, BOBO-1 iodide, SYBR® Green, SYTO61, POP-1, BOBO-3, GelGreen™, EvaGreen™, GelStar™, and ethidium bromide were screened for affinity with scale inhibitors SI-X, SI-A, SI-B, and SI-C under conditions similar to example 1. EvaGreen™, SYBR® Gold, GelStar™, GelGreen™ 3, and ethidium bromide showed brightly colored wells, indicating the formation of fluorescent complexes.

Evaluation of EvaGreen™, SYBR® Gold, GelStar™, GelGreen™ 3, and ethidium bromide continued using DI water, synthetic field brine A and scale inhibitors SI-X, SI-A, SI-B, and SI-C. Ethidium bromide and EvaGreen™ fluoresced without scale inhibitor being present. GelGreen™ 3 showed poor affinity to SI-B and SI-C in DI water. SYBR® Gold and GelStar™ showed good affinity to all the tested scale inhibitors. SYBR® Gold-scale inhibitor complex emitted a stronger fluorescence signal compared to GelStar™-scale inhibitor complex.

The fluorescence of all the scale inhibitor-dye complexes, except ethidium bromide, was completely quenched by the salt in the synthetic brine. This shows that the fluorescent techniques cannot be used without a de-salting method or a method such as capillary electrophoresis that separates the salts from the fluorescent complex.

Sample 3

Several fluorescent internal standards were evaluated, including fluorescein (FL), fluorescein sulfonate (FLS), sulfonated pyrene, calcein, and BCECF. In all cases, the ratio of the scale inhibitor peak height to the internal standard peak area was used for evaluation.

Figure 3:
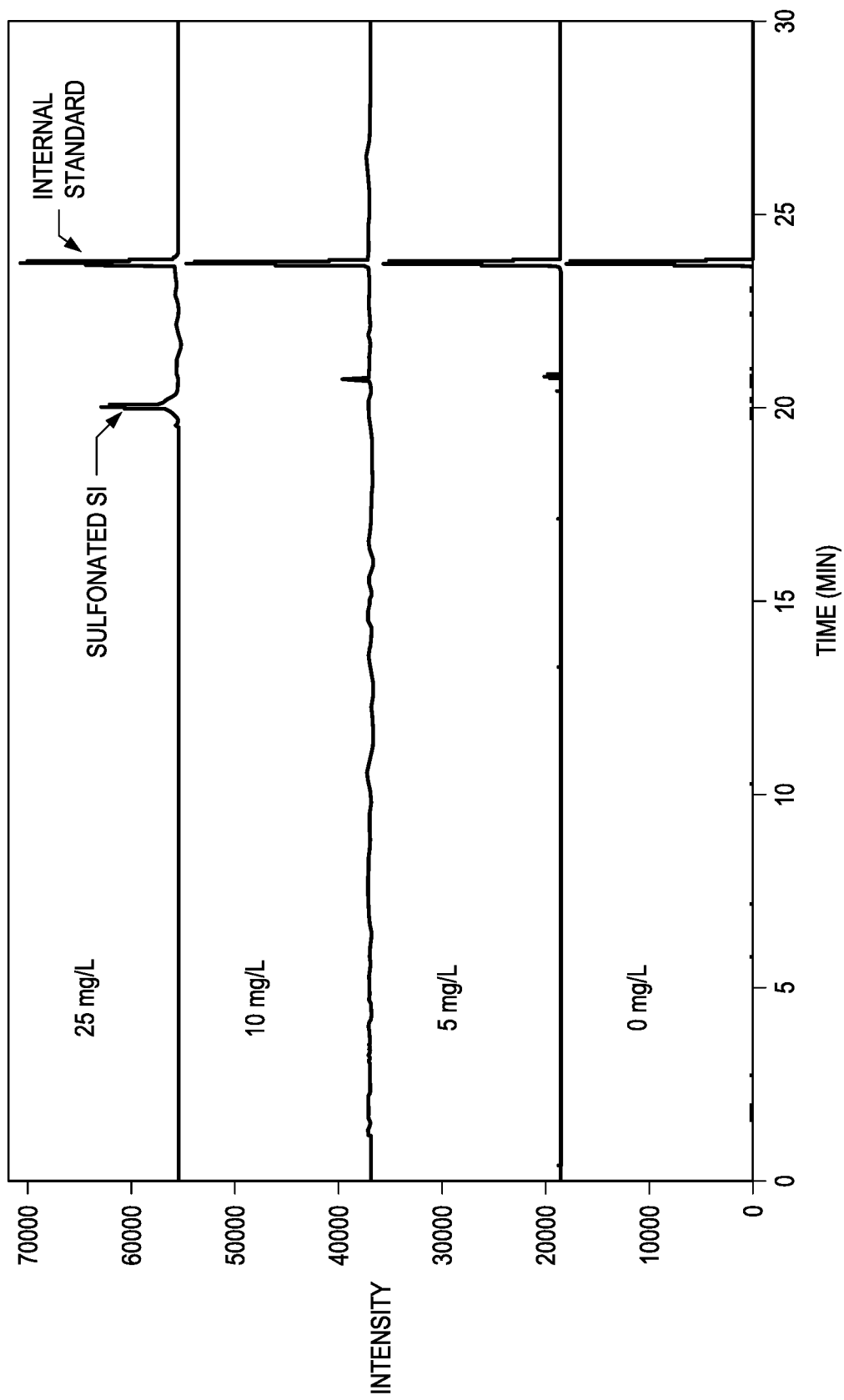
FIG. 3 shows capillary electrophoresis chromatographic overlay of samples containing different amounts of sulfonated scale inhibitors.

All capillary electrophoresis experiments exhibited a Beer-Lambert (linear) relationship to the scale inhibitor-SYBR® Gold complex fluorescent emission and the scale inhibitor concentration up to the saturation. The capillary electrophoresis overlay shows the relationship in FIG. 3.

Sample 4

Two produced water samples were spiked with SI-X. The average measured value of six replicates with 5 and 10 ppm SI-X spiked produced water was 5.3 and 9.7 mg SI/L with standard derivations of 0.4 and 1.3 mg SI/L, respectively.

All ranges disclosed herein are inclusive of the endpoints, and the endpoints are independently combinable with each other. "Or" means 'and/or.' As used herein, "combination" is inclusive of blends, mixtures, alloys, reaction products, and the like. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. The modifier "about" used in connection with a quantity is inclusive of the stated value and has the meaning dictated by the context (e.g., it includes the degree of error associated with measurement of the particular quantity).

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. A method for determining a concentration of a scale inhibitor in a water system, the method comprising:
   contacting a sample of water containing scale inhibitor with a dye in a capillary channel to form a complex effective to generate fluorescence;
   measuring a fluorescence signal generated by the complex; and
   determining a concentration of the scale inhibitor based on the fluorescence signal.

2. The method of claim 1, further comprising separating the scale inhibitor from an inorganic salt contained in said sample of water in the capillary channel before forming the complex.

3. The method of claim 1, wherein the scale inhibitor comprises an anionic scale inhibitor.

4. The method of claim 1, wherein the scale inhibitor comprises a phosphate ester; a phosphonate; a polycarboxylate; a phosphine polymer; a sulfonate; polyvinyl sulfate; or a combination comprising at least one of the foregoing.

5. The method of claim 1, wherein said sample of water comprises less than about 15 weight percent (wt %) of sodium chloride, sodium acetate, and sodium sulfate, or a combination thereof, wherein said wt % is based on a total weight of said sample of water.

6. The method of claim 1, further comprising the step of diluting said sample of water so that the concentration of sodium chloride, sodium acetate, and sodium sulfate, or a combination thereof is less than 15 weight percent (wt %) before said measuring step, wherein said wt % is based on a total weight of said sample of water.

7. The method of claim 1, wherein said water sample is from a water system that is an oilfield fluid comprising seawater, formation water, produced water, a drilling fluid, a completion fluid, a stimulating fluid, a squeezing fluid, or a combination comprising at least one of the foregoing.

8. The method of claim 1, further comprising filling the capillary channel with an electrolyte, and introducing said water sample comprising the scale inhibitor to the capillary channel filled with the electrolyte.

9. The method of claim 8, wherein the electrolyte comprises a buffer salt and a polymer.

10. The method of claim 8, wherein the electrolyte has a pH of about 7 to about 10.

11. The method of claim 8, wherein the electrolyte further comprises an amino acid.

12. A method for determining a concentration of a scale inhibitor in a water system, the method comprising:
   providing a capillary channel having an inlet end and an outlet end, wherein the capillary channel is filled with an electrolyte comprising a buffer salt, a polymer, and a dye;

loading a sample containing a scale inhibitor into the capillary channel from the inlet end;

forming a fluorescent complex of the scale inhibitor and the dye;

measuring a fluorescence signal generated by the complex; and determining the concentration of the scale inhibitor based on the fluorescence signal.

13. The method of claim 12, further comprising separating the scale inhibitor from a salt in the sample before forming the complex.

14. A method of treating a water system, the method comprising:

introducing an effective amount of a scale inhibitor to a water system;

obtaining a sample of the water system containing the scale inhibitor;

contacting the scale inhibitor in the sample with a dye in a capillary channel to produce a complex effective to generate fluorescence;

measuring a fluorescence signal generated by the complex;

determining a concentration of the scale inhibitor based on the fluorescence signal; and adding an additional quantity of a scale inhibitor to the water system if the measured concentration is below a given value.

15. The method of claim 14, further comprising separating the scale inhibitor from a salt in the sample before forming the complex.

16. The method of claim 14, wherein the scale inhibitor comprises an anionic scale inhibitor.

* * * * *